United States Patent [19]

Bijl

[11] Patent Number: 5,955,321
[45] Date of Patent: Sep. 21, 1999

[54] PRODUCTION AND USE OF COMPOSITIONS COMPRISING HIGH CONCENTRATIONS OF VITAMIN B12 ACTIVITY

[75] Inventor: Hendrik Louis Bijl, Vlaardingen, Netherlands

[73] Assignee: Gist-Brocades, Delft, Netherlands

[21] Appl. No.: 08/909,715

[22] Filed: Aug. 12, 1997

[30] Foreign Application Priority Data

Aug. 12, 1996 [NL] Netherlands .......................... 96202254
Jan. 14, 1997 [NL] Netherlands .......................... 97200054

[51] Int. Cl.⁶ .............................. C12P 19/42; C12N 1/20
[52] U.S. Cl. ........................... 435/86; 435/170; 435/822; 514/52; 536/26.4; 536/26.41; 536/26.42
[58] Field of Search ............................ 435/86, 170, 822; 536/26.4, 28.41, 26.42; 514/52

[56] References Cited

U.S. PATENT DOCUMENTS

| | | | |
|---|---|---|---|
| 4,544,633 | 10/1985 | Kojima et al. ............................. | 435/86 |
| 4,659,661 | 4/1987 | Szelmer .................................... | 435/86 |
| 5,338,418 | 8/1994 | Hirayama et al. ..................... | 536/26.41 |
| 5,545,538 | 8/1996 | Ashai et al. ............................... | 435/86 |

OTHER PUBLICATIONS

Chemical Abstracts Caplus 1983:486599 Adrian et al "Industrial biosynthesis of vitamin B12 for veterinary uses" RO 77658, Mar. 30, 1982.
Chemical Abstracts Caplus 1988:628620 Yukitomo et al. "Preparation of microbiol protein containing vitamin B12 and fermented milk . . . " Bitamin (1988)62(10) 565–9, 1988.
Chemical Abstracts Caplus 1995:478531 Kim et al. "Effects of supplemented factors on the production of vitiamin B12 by *Propionibacterium shermani*" Yakhak Hoechi (1994) 38(5) 614–20, 1994.
Chemical Abstracts Caplus 1971:528478 Abou–Zeih et al "Fermentation production of tetracyclines, the antifungal antibiotic, ayf, and vitamin B12 by *Streptomyces aureofaciens*" Pak. J. Sci. Ind. Res. (1971).

Chemical Abstracts Caplus 1974:474484 Adams et al "Separation of free and bound vitamin B12" Brit. J. Haematol. (1974) 26(4) 581–92, 1974.
Saburo et al., "Production of Vitamin B12 by Methanol–assimilating Bacteria," *Chemical Abstracts*, vol. 83, No. 5, p. 363 (Aug. 4, 1975), Ab. No. 4143b.
Tanaka et al., "Production of Vitamin B12 by Methanol–assimilating Bacteria," *J. Ferment. Technol.*, vol. 52, No. 12, pp. 921–924 (1974).
Kvasnikov et al., "Synthesis of B vitamins by bacteria of the genus Arthobacter," *Chemical Abstracts*, vol. 84, No. 3, p. 220 (Jan. 19, 1976) Abs. No. 84:14412g.
Morikawa et al., "Utilization of Hydrocarbons by Microorganisms," *J. Ferment. Technol.*, vol. 47, No. 8, pp. 470–477 (1969) (abstract included on p. 470).
Fujii et al., "Studies on the Formation of Vitamins and their Functions in Hydrocarbon Fermentation," *Hskko Kogsku Zasshi*, vol. 44, No. 4, pp. 185–191 (1966) (abstract included on p. 185).
Schliwa et al., "Stabilization of the cytoplasmic ground substance in detergent–opened cells and a structural and biochemical analysis of its composition," *Proc. Natl. Acad. Sci.*, vol. 78, No. 7, pp. 4329–4333 (Jul., 1981).

*Primary Examiner*—Herbert J. Lilling
*Attorney, Agent, or Firm*—McDonnell Boehnen Hulbert & Berghoff

[57] ABSTRACT

The present invention provides a process for the preparation of a composition comprising natural vitamin B12, wherein said process comprises the steps of:

a) obtaining microbial cells containing natural vitamin B12, b) causing opening of the microbial cells such that at least part of the soluble content of the cells comprising vitamin B12 is released in a liquid in which the cells are contained, c) separating the opened cells and the liquid comprising the vitamin B12, d) preparing a mixture of the vitamin B12 and at least a part of the opened cells, wherein the mixture has a vitamin B12 concentration on dry matter in excess of 0.1% (w/w).

38 Claims, 1 Drawing Sheet

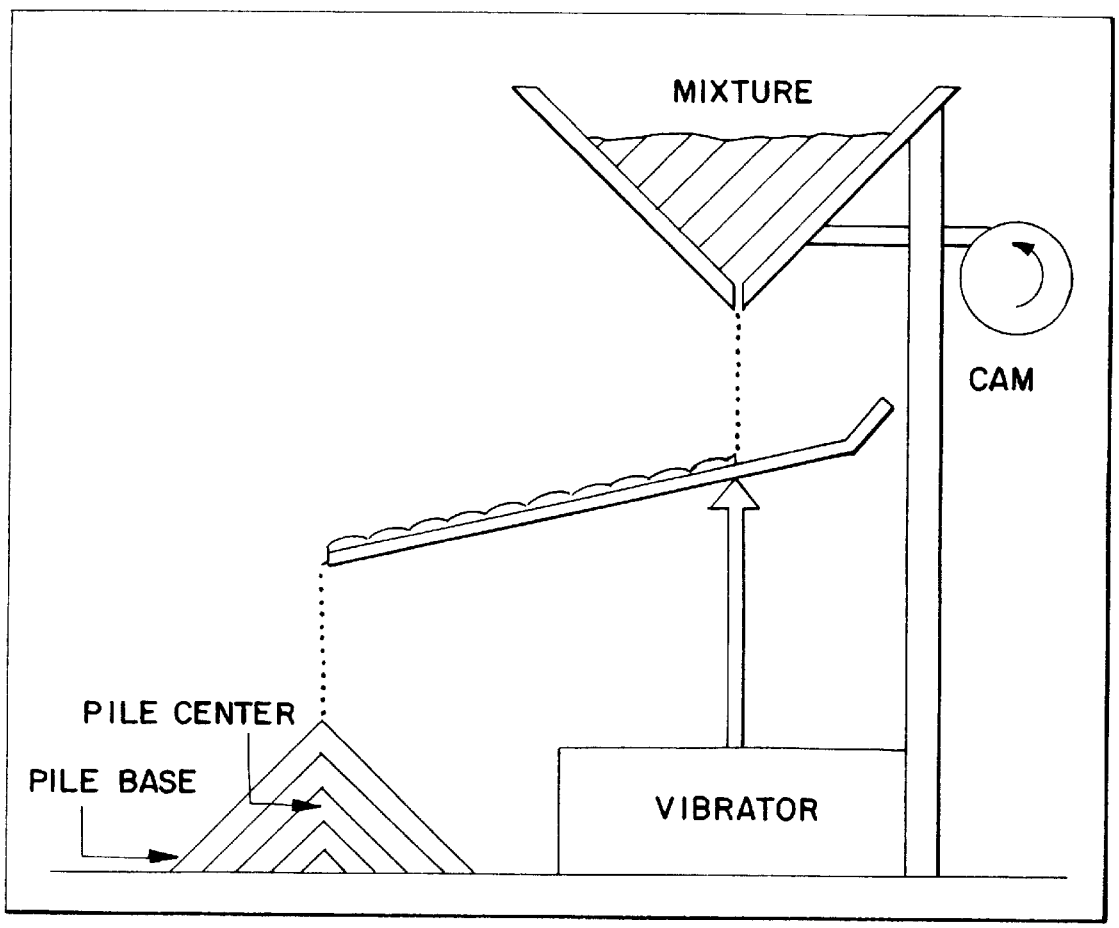

PRODUCTION AND USE OF COMPOSITIONS COMPRISING HIGH CONCENTRATIONS OF VITAMIN B12 ACTIVITY

FIELD OF THE INVENTION

The present invention relates to the production of compositions comprising natural vitamin B12.

BACKGROUND OF THE INVENTION

Vitamin B12 is an important vitamin for humans and animals It is used to treat pernicious anaemia, and peripheral neuritis, and is used as a dietary supplement. Vitamin B12 is also an important animal feed supplement as growth enhancer.

The term vitamin B12 is used to describe compounds of the cobalt corrinoid family, in particular those of the cobalamin group. The most used compound of this group is cyanocobalamin and as such the term vitamin B12 is sometimes used to refer to cyanocobalamin. In this specification the term vitamin B12 should be attributed its broad meaning so as to include all the cobalt corrinoids of the cobalamin group, which include in particular cyanocobalamin, hydroxocobalamin, methylcobalamin and 5' desoxyadenosylcobalamin characterized by a cyano, hydroxyl, methyl or 5'-desoxyadenosyl radical respectively. The methylcobalamin and 5'desoxyadenosylcobalamin compounds are known to be unstable to light in isolated form and are easily transformed to hydroxocobalamin in aqueous solution. For this reason, almost all commercial vitamin B12 preparations consist of the stable cyanocobalamin which as such is not the chemical form in which vitamin B12 can be found in nature. In this specification the term natural vitamin B12 is defined so as to comprise all chemical forms of vitamin B12 naturally occurring in nature, cyanocobalamin thus being excluded.

Vitamin B12 is produced industrially by microbial fermentation, using almost exclusively *Pseudomonas denitrificans* and Propionibacterium species, then converting the natural vitamin B12 into the cyanocobalamin form by chemical processes including cyanidization followed by extraction and purification steps using organic solvents (as reviewed by Spalla et al, 1989 "Microbial production of vitamin B12", In: Biotechnology of vitamins, pigments and growth factors, E. J. Vandamme ed., Elsevier, London, New York, pp. 257–284). The chemical conversion step and any subsequent purification steps cause this production process to be expensive, unsafe to the operators and environmentally unfriendly.

Upon ingestion, animals and humans convert cyanocobalamin to one of the natural forms of vitamin B12 such as methylcobalamin or 5'-desoxyadenosylcobalamin which are required to function as a coenzyme for several biochemical conversions (Ellenbogen, L., in: Handbook of vitamins. Nutritional, biochemical and clinical aspects; ed; L. J. Machlin, Marcel Dekker Inc., New York and Basel) In addition efficient growth of animals requires the presence of a sufficient amount of vitamin B12 activity in the animal feed. Vitamin B12 preparations are frequently sold as feed supplements as such or as part of a premix containing additional vitamins and other feed additives.

It is clear therefore that a direct supply of 5'-desoxyadenosylcobalamin or methylcobalamin instead of cyanocobalamin would be of benefit. In view of the instability of these two compounds they are not produced in isolated form but are produced in dry formulation together with the biomass of the organism in which they are produced. Such formulations are well suited for use as animal feed supplement. For the production of methylcobalamin and 5'desoxyadenosylcobalamin, bacteria of the genus Propionibacterium are most preferred, because, unlike *P. denitrificans*, bacteria of this genus have obtained the GRAS (Generally Recognized As Safe) status from the U.S. Food and Drug Administration and are not known to produce endotoxins. Propionibacterium species are aerotolerant, nonmotile, nonsporulating, Gram-positive bacteria characterized further by the production of large amounts of propionic acid from carbohydrates, lactic acid and polyhydroxy alcohols. The genus Propionibacterium falls into the high "GC" subdivision of the Gram-positive bacteria (T. D. Brock, M. T. Madigan, J. M. Martinko and J. Parker in: The Biology of Microorganisms 7th Edition, Prentice-Hall International is Inc., 1994).

Patent application RU 2001953 (Antibiotics Enzymes Research Technical Institute) refers to a spray-drying method for *Propionibacterium shermanii* which has been used to produce 5'-desoxyadenosylcobalamin-containing biomass. Methylcobalamin in biomass from methanogenic bacteria is commercially available from the Gedeon Richter company. However, the vitamin B12 content in these preparations is limited by the level at which the vitamin B12 is produced during fermentation and, as a consequence, the vitamin B12 content in these preparations does not exceed 0.1% (w/w) The concentration of vitamin B12 in a composition is customarily measured as the dry weight of vitamin B12 as a percentage of the dry weight of the composition.

Concentrated (i.e. >0.1% w/w) products of cyanocobalamin are commercially available However, feed mills and premix manufacturers cannot use this material because as a consequence of its electrostatic properties cyanocobalamine segregates from its carrier upon processing in feed mills and premix manufacturers when formulated at concentrations>0.1% w/w. Segregation is a particular problem during sieving, wind sifting or allowing the composition to stand for a prolonged period time.

Given these difficulties encountered in the prior art, a need remains for improved methods for the production as well as use of compositions comprising high concentrations of vitamin B12 activity. The present invention thus seeks to provide such improved methods which avoid if not completely overcome some of the problems of the prior art. In particular, it is an object of the present invention to provide a process for isolating natural vitamin B12 in relatively concentrated form. These new concentrated products preferably can be used, for example, in animal feed, particularly human food, or as an ingredient in cosmetics, The new products may be more convenient to use and to transport (i.e., inasmuch as they are concentrated), thus allowing a reduction in costs. They may advantageously be used by feed mills and premix manufacturers as they show reduced segregation of the vitamin B12 from the carrier during processing. Moreover, the process can be carried out on an industrial scale and is relatively environmentally friendly, as there is no need to use organic solvents or cyanidation. These and other objects and advantages of the present invention, as well as additional inventive features, will be apparent from the description of the invention provided herein.

SUMMARY OF THE INVENTION

The present invention provides, among other things, a process for isolating natural vitamin B12, the product (e.g., composition) obtained thereby, and methods of using the product, for instance, as a food supplement or cosmetic preparation. In particular, the present invention preferably provides a process for isolating natural vitamin B12 wherein a composition obtained by this process comprises natural vitamin B12 in an amount greater than 0.1% (w/w) based on the dry matter content of the composition. Desirably, the natural vitamin B12 obtained by the process according to the invention is distributed substantially homogeneously throughout the composition, and does not segregate from other components of the composition, for example, when exposed to sieving, wind, sifting, gravitational forces, or electrostatic forces.

BRIEF DESCRIPTION OF THE DRAWING

FIG. 1 depicts the separation test employed to confirm the absence of segregation from carrier of vitamin B12 isolated according to the invention.

DETAILED DESCRIPTION OF THE INVENTION

The present invention provides a process for preparing natural vitamin B12, the composition produced thereby, and the use of the composition, for instance, as a food supplement (particularly a food supplement employed to promote the growth of an animal such as a human) or, in the production of a cosmetic preparation (e.g., a preparation that is applied topically), as further described herein. In particular, the invention preferably provides a process for isolating natural vitamin B12 comprising (a) culturing microbial cells capable of producing natural vitamin B12 under conditions such that the cells produce natural vitamin B12 intracellularly, and (b) disrupting the outer membrane of the cells such that the natural vitamin B12 is released from the cells. Preferably the composition isolated by this process has a relatively high concentration (>0.1% w/w) of natural vitamin B12.

Desirably, the process is carried out wherein the cells are opened in step (b) such that at least part of the soluble content of the cells comprising vitamin B12 is released into a liquid in which the cells are contained. Optimally, in still further steps, the opened cells are separated from the liquid comprising the vitamin B12, and a mixture is prepared of the vitamin B12 and at least a part of the opened cells.

The microbial cells containing vitamin B12 are preferably obtained in an industrial fermentation process using a microorganism known to produce vitamin B12. These include bacterial belonging to the genera of Acetobacterium, Aerobacter, Agrobacterium, Alcaligenes, Arthrobacter, Azotobacter, Bacillus, Clostridium, Corynebacterium, Eacherichia, Eubacterium, Flavobacterium, Methanobacillus, Methanosarcina, Mycobacterium, Propionibacterium, Proteus, Pseudomonas, Rhizobium, Rhodopseudomonas, Salmonella, Serratia, Streptococcus, Streptomyces and Xanthomonas Preferably the bacterium to be used in the process of the invention is safe for consumption by humans and/or animals and does not produce endo- or exotoxins. More preferably the bacterium has obtained the GRAS (Generally Recognized As Safe) status from the U.S. Food and Drug Administration. The most preferred bacterium for use in the process of the invention is of the genus Propionibacterium, the preferred species of which are *P. freudenreichii* or *P. shermanii*.

It is well known to persons skilled in the art that the industrial production of vitamin B12, like that of many other microbial metabolites, is carried out using strains resulting from programs designed to improve the desired qualities of any particular strain. These programs consist essentially of the treatment of the production strain with a mutagenic agent and the selection of mutants exhibiting an improved productivity or other advantages. Several techniques have been described for the rational selection of vitamin B12 overproducing mutant microorganisms (Spalla, C., Grein, A., Garofo, L and Ferni, G. Microbial production of vitamin B12 In: Biotechnology of vitamins, pigments and growth factors pp. 257–284 (E. J. Vandamme, ed.) Elsevier, London/NY, 1989). Such mutant strains are used in preferred processes of the invention and are capable of further increasing the vitamin B12 concentrations in the compositions obtained.

In the invention the term "natural vitamin B12" is defined so as to comprise all chemical forms of vitamin B12 naturally occurring in nature, the cyanocobalamin form of vitamin B12 being excluded. In the preferred processes and compositions of the invention the natural vitamin B12 comprises 5'-desoxyadenosylcobalamin and/or methylcobalamin.

In the process of the invention the microbial cells containing vitamin B12 are treated so as to cause lysis or other disruption of the cell membrane. Lysis describes the opening of the microbial cells such that (at least part of) the soluble content of the cells comprising the vitamin B12 is released into a liquid in which the cells are contained. Preferred treatments for opening the cells are heat treatments including pasteurization or heating in an autoclave; treatment with bacteriolytic enzymes such as lysozyme; mechanical disruption of the cells including grinding or the use of shear forces; treatment with chemicals which cause cell lysis such as detergents or organic solvents; as well as combinations of these treatments. The lysis or other membrane disruption produces a lysate which can be separated is into solid and liquid phases.

In a preferred process of the invention at least part of the solid phase (opened cells) is added to the liquid phase containing the natural vitamin B12 so that a composition is obtained which is a mixture comprising biomass, i.e. preferably opened microbial cells, and natural vitamin B12. The vitamin B12 content or concentration of these compositions is expressed as weight-percentage of vitamin B12 based on the dry matter content of the composition.

The process of the invention produces compositions having a vitamin B12 concentration in excess of 0.1% w/w) on dry matter. In preferred processes the composition has a natural vitamin B12 concentration in excess of 0.2% (w/w), more preferably in excess of 0.4% (w/w), still more preferably in excess of 0.6%, still more preferably in excess of 0.8% (w/w), and most preferably in excess of 1.0% (w/w). It is preferable that vitamin B12 concentrations of the compositions of the invention do not exceed 10% (w/w), more preferably the vitamin B12 concentrations do not exceed 5%.

In the process of the invention the solid phase of the lysate comprising the cell debris resulting from opening the cells is separated from the liquid containing the released vitamin B12. A number of different solid-liquid separation techniques are available to the skilled person for performing this separation, including centrifugation and filtration techniques. A preferred method for separating the solid cell debris from the vitamin B12 containing liquid is ultrafiltration.

In a preferred process of the invention the opened microbial cells are washed and the washings are combined with the vitamin B12 obtained after separation of the cells and the vitamin B12 containing liquid. Preferably the washing is effected by diafiltration with ion-free water being preferably used for washing the opened cells. The vitamin B12 containing diafiltrate is then combined with the vitamin B12 containing liquid phase.

In a preferred process of the invention further the natural vitamin B12 containing liquid phase is subjected to a drying treatment. Any suitable means of drying can be used such as e.g. spray-drying, fluid-bed drying, freeze drying, or drying in vacuum.

In a preferred process of the invention, the microbial cells containing vitamin B12 are washed prior to undergoing lysis, so as to further increase the vitamin B12 concentration on dry matter by removing medium components. Preferably said washing is performed using diafiltration whereby preferably using ion-free water.

In a further aspect invention provides compositions comprising vitamin B12, which are obtainable in a process of the invention. Preferably the majority of the vitamin B12 activity in these compositions is in the form of natural vitamin B12. Compositions of the invention are characterized in that the vitamin B12 is present in a concentration based on dry matter in excess of 0.1% (w/w) In a preferred composition of the invention the vitamin B12 concentration is in excess of 0.2% (w/w), preferably in excess of 0.4% (w/w), more preferably in excess of 0.6%, still more preferably in excess of 0.8% (w/w), and most preferably in excess of 1.0% (w/w). However, preferably the vitamin B12 concentrations of the compositions of the invention do not exceed 10% (w/w), more preferably the vitamin B12 concentrations do not exceed 5%. The compositions of the invention comprise vitamin B12 and a carrier which preferably comprises biomass e.g. whole cells and/or cell debris. The biomass comprised in these compositions is preferably derived from a microorganism capable of producing vitamin B12, such as the bacteria mentioned above, of which the Propionibacterium species are most preferred.

The compositions of the invention are preferably dry compositions, wherein dry is defined as having a water content of less than 15% by weight, more preferably less than 10%, most preferably less than 5%.

In preferred dry compositions of the invention the vitamin B12 activity is distributed substantially homogeneously throughout the powder or granulated powder containing the carrier and the vitamin B12. As result, the vitamin B12 activity in these compositions advantageously does not segregate to a large extent from the other constituents in the composition, especially when exposed to gravitational forces, sieving, wind sifting or electrostatical forces during processing of the compositions, even when used at concentrations in excess of 0.1% (w/w). Processing is herein understood to comprise processing of the compositions of the invention into feed and feed premixes.

In a further aspect of the invention, the composition of the invention is used as or in the production of growth promoting feed supplement for animals. To this end the compositions containing vitamin B12 are added to the other feed components, either directly or in the form of a premix which also contains other vitamins, minerals and/or bioactive ingredients. As shown in the specific example, feeding an animal a diet comprising a composition of the invention promotes its growth.

In a still further aspect of the invention the compositions comprising vitamin B12 are used as or in the production of a human food supplement and/or are incorporated into cosmetic preparations, such as shampoos or body lotions.

In particular, such a food supplement as set forth herein can be employed to promote the growth not only of humans, but also, of other animals including, but not limited to, an amphibian, bird, insect, reptile, or mammal other than human. Preferably the mammal is a human, rodent, primate (such as chimpanzee, monkey, age, gorilla, orungantun, or gibbon), feline, canine, or ungulate (such as ruminant or swine).

Similarly, a cosmetic preparation as set forth herein preferably is a preparation that is applied topically to the hair, skin, lips, or nails of a mammal, preferably a human. For instance, the vitamin B12 solution optimally can be incorporated in any preparation that is employed to liberally contact the surface of an organism. In particular, such a cosmetic preparation includes, but is not limited to: makeup such as foundation, eye shadow, eye liner, mascara, lipgloss, lipstick, lipliner, face powder, blush; hair products including shampoo, conditioner, hair setting lotion or tonic, hair spray or gel, pomades, and the like; body lotion, salves or creams employed for moisturizing, self-tanning, suntanning, after tanning, facilitation of wound healing, anti-aging, and as topical analgesics; nail products such as nail creams (e.g., employed for nail strengthening or moisturizing, or as antifungal agents), nail polish, and nail polish remover.

Moreover, the food supplement and/or cosmetic preparations according to the invention further can comprise other agents, e.g., other agents having a beneficial or therapeutic effect (e.g., growth promotion, moisturizing, etc.), or other agents included merely to change the physical characteristics of the cosmetic preparation or food supplement (e.g., employed as fillers, or to make the product have a more pleasing taste, smell, or appearance). Preferably, however, any such other agents included in the preparations do not negate the beneficial effects obtained with inclusion of vitamin B12.

The following examples further illustrate the present invention and, of course, should not be construed as in any way limiting its scope.

EXAMPLES

Experimental

Vitamin B12 Assay

Vitamin B12 activity was assayed using the turbidimetric bioassay based on the growth response of *Lactobacillus leichmanii* ATCC 7830 as described in detail in: The United Stated Pharmacopoeia, The National Formulary, 1995, pp. 1719–1721, United Stated Pharmacopoeial Convention, Inc., Rockville Md.

Plasma B12 Concentrations

Plasma B12 was measured using a commercially available radioassay kit (Bio-Rad Laboratories Ltd, Hemel Hempstead, UK.). The plasma sample is combined with vitamin $B_{12}(^{57}Co)$ in a solution containing dithiothreitol and cyanide. The mixture is boiled for 30 minutes to inactivate endogenous binding proteins and to convert the various forms of vitamin $B_{12}$ to cyanocobalamin. The mixture is cooled and then combined with immobilised (bound to polymer beads), affinity-purified porcine intrinsic factor. This adjusts and buffers the pH of the reaction mixture to 9.35. The reaction mixture is then incubated for 60 minutes at room temperature. During incubation, the endogenous and labelled vitamins compete for the limited number of binding sites based on their relative concentrations. The reaction mixture is then centrifuged at 1500 g for 10 minutes. The labelled and unlabelled vitamins binding to the immobilised binding proteins are concentrated at the bottom of the tube in the form of a pellet and the unbound vitamins remain in the supernatant. The supernatant is aspirated off and the radioactivity associated with the pellet is counted. Standard curves are prepared using vitamin $B_{12}$ standards in a human serum albumin base. The concentration of vitamin $B_2$ in the plasma sample is determined from the standard curves. Standard curves were plotted and unknowns determined using the AssayZap universal assay calculator, version 2.32 (Biosoft, Cambridge, UK.).

Plasma samples required to be diluted 10–50 fold to bring them within the most sensitive range of the assay.

Example 1

A fermentation was performed with *Propionibacterium freudenreichii* using a process known to those skilled in the art (see e.g. Spalla et al, 1989 "Microbial production of vitamin B12", In: Biotechnology of vitamins, pigments and growth factors, E. J. Vandamme ed., Elsevier, London, New York, pp. 257–284). A suitable *P. freudenreichii* strain is available from the American Type Culture Collection under accession number ATCC 6207. A broth was obtained at the end of the fermentation which had a 5'-desoxyadenosylcobalamin potency of 10 mg/l and with a dry matter content of 7.5%. Spray-drying of this broth resulted in a product with a vitamin B12 concentration of 0.01%.

In order to obtain a higher vitamin B12 concentration, a solid-liquid separation of the broth was attempted Vitamin B12 is intracellular in *P. freudenreichii*, for which reason removal (extracellular) medium components and subsequent spray-drying of the biomass should result in a spray-dried product with a higher vitamin B12 concentration On lab scale a centrifugation step was performed at a maximal g-force of 5000–6000×g. This g-force is comparable with the centrifugal forces of centrifuges that are used on industrial scale. Aliquots of 1000 ml broth were centrifuged in a Beckmann JM/6E centrifuge during 10 minutes at 5000 rpm. However, no separation of biomass and broth was obtained under these conditions.

Because higher centrifugal forces are less attractive on an industrial scale for economic reasons, we tested whether it is feasible to separate the liquid and solids in the broth using ultrafiltration.

2000 ml of broth, with an initial concentration of 4.5 mg vitamin B12/l (vitamin B12 on dry matter 0.02%), was ultrafiltered by means of a 30 kD AMICON spiral wound module (0.09 $m^2$) with a feed pressure of 1 bar. Under these conditions it was possible to concentrate the sample of vitamin B12 5 times. The average permeateflux was 30 $l/m^2h$. The vitamin B12 concentration in the concentrate was 20 mg/l, whereas in the permeate less than 0.2 mg/l vitamin B12 was detected. The vitamin B12 concentration in the concentrate, when expressed in terms of dry matter content, was 0.05%, compared to 0.2% prior to ultrafiltration.

To further increase the titre of vitamin B12 on dry matter, we next tested diafiltration of the biomass.

The ultrafiltration concentrate as obtained in the above described experiment was washed six times with ion-free water, which resulted in a vitamin B12 potency in the concentrate of 20 mg/l. In the diafiltrate no vitamin B12 activity was detected. Subsequent spray-drying of the concentrate resulted in a spray-dried product with a vitamin B12 concentration of 0.06%.

We conclude from the above experiments that it is not possible to obtain a product with a vitamin B12 concentration of more than 0.06% based on dry matter starting from a broth with a vitamin B12 titre of 5–10 mg/l.

Example 2

In order to prevent the presence of viable production organisms, i.e. live cells, in the dried product, a pasteurisation step of 65° C. for 30 minutes was performed on a broth which was obtained as described in Example 1. The treated broth was ultrafiltered as described above.

A pink coloured permeate was observed with a vitamin B12 concentration (by dry matter) of 0.2–0.4%. The pasteurization is thought to cause lysis of (at least part of) the *P. freudenreichii* cells and release of the intracellular vitamin B12 into the medium. This can allow one to obtain dried products comprising vitamin B12 in concentrations ranging from 0.06% to 0.3% (based on dry matter), by combining the permeate and the pasteurised broth prior to spray-drying.

In more detail, 350 ml of the heat-treated broth was ultrafiltered under the conditions described above in Example 1. The concentrate was diafiltered with 2500 ml ion-free water. The clear pink coloured permeate and diafiltrate were combined and mixed with 750 ml pasteurised ultrafiltration concentrate. The mixture was spray-dried in a lab Buchi spray-dryer whereby the inlet temperature was set at 180° C. and the outlet was set at a temperature of 104° C. The vitamin B12 concentration of the thus obtained spray-dried product was 0.13%

Example 3

1200 l of broth with a vitamin B12 concentration of 8 mg/l was obtained in a pilot plant fermentation of *P.freudenreichii* and was ultrafiltrated in a DDS ultra filtration module M37 using 20 kD membranes and an initial waterflux of 38 $l/m^2h$. The temperature during ultrafiltration was kept ambient. The circulation flow was about 15 $m^3/h$. The feed pressure was set at about 7 bar. The broth was concentrated 11.5 times (average flux of 23 $l/m^2h$). The concentrate was washed with 500 l of ion-free water at ambient temperature till a conductivity of about 3 mS/cm was reached.

The resulting concentrate was treated at 90° C. for 6 hours. Part of the heat-treated concentrate was diafiltered, resulting in about 300 l of vitamin B12 containing permeate. The retentate was stored at 4° C.

The permeate was concentrated on a pilot scale in a glass evaporator at 40° C. under vacuum, resulting in about 6 l of concentrate.

By combining and mixing an appropriate amount of the retentate with the concentrated permeate, we composed a mixture which was spray-dried in a NIRO spray-dryer. The air temperature at the inlet was set at 160° C. and the outlet temperature was regulated at about 90–95° C. In 5 hours operation time about 45 l of the mixture was spray-dried (about 9 kg/hour). This resulted in 1307 g of spray-dried material with a vitamin B12 activity of 1100 mg/kg, i.e. 0.11%.

Example 4

In an experiment similar to the one as described in Example 3, a fermentation was performed using the improved *P.freudenreichii* strain CBS 929.97. The resulting vitamin B12 concentration in the fermentation broth was 40 mg/l. The ultrafiltration and diafiltration were essentialy performed as described in Example 3.

Using ultrafiltration, 100 l of the 40 mg/l broth was concentrated to about 40 l. Using diafiltration, the concentrate was washed with 200 l of ion-free water. The resulting washed concentrate had a vitamin B12 activity of 96.5 mg/kg and 6.72% of dry matter (spray drying of this washed concentrate would have given a vitamin B12 activity of 0.14%).

The washed concentrate was subsequently lysed at 90° C. for 5 minutes, followed by a separation of cell debris and liquid by ultrafiltration. The potential vitamin B12 concentration of the permeate reached of 0.87% at dry matter (calculated from a vitamin B12 activity of 52.1 mg/kg and a dry matter content of 0.6%). After preconcentration of the permeate in vacuum at 65° C., different amounts of permeate and concentrate were combined and dried. The vitamin B12 potencies of the obtained dried products were as given below:

| concentrate:permeate | vitamin B12 activity by dry matter |
|---|---|
| 1:1 | 0.5% |
| 3:7 | 0.65% |
| 2:8 | 0.72% |
| 8:2 | 0.29% |

*P.freudenreichii* CBS 929.97 was deposited Jul. 10, 1997 at the Centraalbureau voor Schimmelcultures, Oosterstraat 1, Postbus 273, NL-3740 AG Baarn, The Netherlands.

Example 5
Application of Natural Vitamin B12 in Animal Feed

A trial was performed with broilers to compare the efficacy of natural vitamin B12 with cyanocobalamin. One day old male broilers were randomly assigned to cages. Eight animals were kept per cage. The cages were situated in an artificial heated, ventilated and illuminated broiler house. The animals were vaccinated against New Castle disease at ages one and fourteen days. The animals received the experimental diets ad libitum from day 1, the first 10 days in the form of crumbles, later in the form of pellets. Water was available freely. The experiment lasted 28 days. At day 28 the animals were weighed, feed consumption determined and blood samples were taken. The blood samples were taken from 4 randomly selected broilers per cage. Blood was collected in heparinised tubes. The tubes were centrifuged and the plasma was frozen (−18° C.) until vitamin B12 analysis was carried out. This analysis was performed as described above under Experimental (Plasma B12 concentrations).

Three treatments were comprised in this experiment:
I. Basal diet without addition of vitamin B12
II. Basal diet with addition of cyanocobalamin (30 ppb active substance)
III. Basal diet with addition of natural vitamin B12 (30 ppb active substance)

Each treatment was replicated 5 times.

The composition of the basal diet is presented in table 1, the results in table 2.

Table 1. Composition of the basal diet (in %).

TABLE 1

| Composition of the basal diet (in %). | |
|---|---|
| Maize | 55 |
| Tapioca | 1 |
| Soybeanmeal | 30 |
| Soybeans, heat treated | 5 |
| Feather meal | 1 |

TABLE 1-continued

| Composition of the basal diet (in %). | |
|---|---|
| Soya oil | 2 |
| Animal fat | 3 |
| Vitamins*, minerals, amino acids | 3 |

*Without vitamin B12.

Calculated contents:

| Metabolic Energy | 13.3 MJ/kg |
|---|---|
| Crude protein | 22.0% |
| Lysine (total) | 1.27% |
| Methionine + Cysteine (total) | 0.95% |

Table 2. Effect of cyanocobalamin and natural vitamin B12 on average growth, feed intake and feed conversion ratio between 1 and 28 days of age and on blood plasma vitamin B12 contents at day 28.

TABLE 2

Effect of cyanocabalamin and natural vitamin B12 on average growth, feed intake and feed conversion ratio between 1 and 28 days of age and on blood plasma vitamin B12 contents at day 28.

| | Growth (g) | Feed intake (g) | Feed Conversion ratio | Bloodplasma Vit. B12 (ng/l) |
|---|---|---|---|---|
| Basal diet | 1139 | 1736 | 1.53 | 14 |
| +Cyanocobalamin | 1264 | 1762 | 1.41 | 32 |
| +Natural vitamin B12 | 1261 | 1771 | 1.40 | 41 |

Example 6
Segregation of Vitamin B12 Activity from a Carrier

Segregation of the active compound from the carrier may be caused by particle shape, density and bulk density, flowability, adhesive and electrostatic properties, moisture content, and hygroscopicity. These segregation processes may occur during manufacturing of premixes and compound feed and during subsequent transport and storage.

This segregation is particularly critical in the case of premixes which comprise microcomponents such as vitamins and trace elements, macrocomponents such as minerals and carriers.

The demixing properties of existing commercial cyanocobalamin preparations (obtained from Rhône-Poulenc under the brandname Microvit® B12) has been compared with natural vitamin B12 preparation prepared as described in example 4. Limestone is used as a carrier for the existing commercial cyanocobalamine preparations.

The test substances were run out of a storage vessel via a vibrating channel to form a pile as shown in FIG. 1.

Three samples were taken from the center and mixed. The procedure was repeated with samples from the base of the pile The samples were analyzed for vitamin B12 activity as described above and compared withe the original homogeneous mix. Deviations in samples from the original homogeneous mix are calculated as follows:

Deviation at base (%)={(concentration as base−concentration original mix)/concentration original mix}*100

Deviation at center (%)={(concentration at center−concentration original mix)/concentration original mix}*100

Comparison of the deviations at the pile base and pile center of compositions of cyanocobalamin and natural vitamin B12 of the invention are shown in Table 3.

TABLE 3

| Test substance | Separation test (%) Pile base | Separation test (%) Pile center |
|---|---|---|
| Cyanocobalamin 0.1% | <+10 | <−10 |
| Cyanocobalamin 1% | +56 | −78 |
| Natural vitamin B12 (0.9%) | +8 | −12 |

All of the references cited herein are hereby incorporated in their entireties by reference.

While this invention has been described with emphasis on preferred embodiments, it will be obvious to those of ordinary skill in the art that the preferred embodiments can be varied. It is intended that the invention can be practiced otherwise is than as specifically described herein. Accordingly, this invention includes all modifications encompassed within the spirit and scope of the appended claims.

What is claimed is:

1. A process for isolating natural vitamin B12 comprising:
   (a) culturing microbial cells capable of producing natural vitamin B12 under conditions such that said cells produce natural vitamin B12 intracellularly;
   (b) disrupting the outer membrane of said cells such that said natural vitamin B12 is released from said cells into the medium in which the cells are cultured to produce a liquid phase containing the natural vitamin B12 and a solid phase; and
   (c) separating the liquid phase from the solid phase to obtain a preparation containing natural vitamin B12.

2. The process according to claim 1, wherein said natural vitamin B12 is any chemical form of vitamin B12 that occurs naturally in nature except for cyanocobalamin.

3. The process according to claim 1, wherein said natural vitamin B12 is selected from the group consisting of hydroxocobalamin, 5'-desoxyadenosylcobalamin, and methylcobalamin.

4. The process according to claim 1, wherein said natural vitamin B12 is 5'-desoxyadenosylcobalamin or methylcobalamin.

5. The process according to claim 1, wherein said cells are selected from the group consisting of cells of the genera Acetobacterium, Aerobacter, Agrobacterium, Alcaligenes, Arthrobacter, Azotobacter, Bacillus, Clostridium, Corynebacterium, Escherichia, Eubacterium, Flavobacterium, Methanobacillus, Methanosarcina, Mycobacterium, Propionibacterium, Proteus, Pseudomonas, Rhizobium, Rhodopseudomonas, Salmonella, Serratia, Streptococcus, Streptomyces and Xanthomonas.

6. The process according to claim 1, wherein said cells are a mixture of cells selected from the group consisting of cells of the genera Acetobacterium, Aerobacter, Agrobacterium, Alcaligenes, Arthrobacter, Azotobacter, Bacillus, Clostridium, Corynebacterium, Escherichia, Eubacterium, Flavobacterium, Methanobacillus, Methanosarcina, Mycobacterium, Propionibacterium, Proteus, Pseudomonas, Rhizobium, Rhodopseudomonas, Salmonella, Serratia, Streptococcus, Streptomyces and Xanthomonas.

7. The process according to claim 1, wherein said cells are of the genus Propionibacterium.

8. The process according to claim 1, wherein said disrupting is done by lysis of said cells.

9. The process according to claim 8, wherein said lysis is done by treatment selected from the group consisting of heat treatment, pasteurisation, treatment with bacteriolytic enzymes, mechanical disruption, and chemical treatment.

10. The process according to claim 8, wherein said lysis is done by a mixture of treatments selected from the group consisting of heat treatment, pasteurisation, treatment with bacteriolytic enzymes, mechanical disruption, and chemical treatment.

11. The process according to claim 8, which further comprises washing said cells prior to said lysis.

12. The process according to claim 11, wherein said washing is done by diafiltration.

13. The process according to claim 1, wherein said preparation of natural vitamin B12 shows reduced segregation of vitamin B12 from the carrier during processing.

14. The process according to claim 1, wherein said separation of said solid and liquid phases is effected by ultrafiltration or microfiltration.

15. The process according to claim 1, which further comprises drying said liquid phase.

16. The process according to claim 1, which further comprises adding at least part of said solid phase to said liquid phase.

17. The process according to claim 1, which further comprises washing said solid phase to obtain washings and combining said washings with said liquid phase.

18. The process according to claim 17, wherein said washing is done by diafiltration.

19. A process for isolating natural vitamin B12 comprising:
   (a) culturing microbial cells capable of producing natural vitamin B12 under conditions such that said cells produce natural vitamin B12 intracellularly;
   (b) disrupting the outer membrane of said cells such that said natural vitamin B12 is released from said cells to produce a liquid phase containing the natural vitamin B12, and a solid phase;
   (c) separating the liquid and the solid phases; and
   (d) adding at least part of said solid phase to said liquid phase to obtain a mixture comprising said natural vitamin B12.

20. The process according to claim 19, wherein the cells are separated from the media in which they are cultured prior to disrupting the outer membrane.

21. The process according to claim 19, wherein said natural vitamin B12 is any chemical form of vitamin B12 that occurs naturally in nature except for cyanocobalamin.

22. The process according to claim 19, wherein said natural vitamin B12 is selected from the group consisting of hydroxocobalamin, 5'-desoxyadenosylcobalamin, and methylcobalamin.

23. The process according to claim 19, wherein said natural vitamin B12 is 5'-desoxyadenosylcobalamin or methylcobalamin.

24. The process according to claim 19, wherein said cells are selected from the group consisting of cells of the genera Acetobacterium, Aerobacter, Agrobacterium, Alcaligenes, Arthrobacter, Azotobacter, Bacillus, Clostridium, Corynebacterium, Escherichia, Eubacterium, Flavobacterium, Methanobacillus, Methanosarcina, Mycobacterium, Propionibacterium, Proteus, Pseudomonas, Rhizobium, Rhodopseudomonas, Salmonella, Serratia, Streptococcus, Streptomyces and Xanthomonas.

25. The process according to claim 19, wherein said cells are a mixture of cells selected from the group consisting of cells of the genera Acetobacterium, Aerobacter, Agrobacterium, Alcaligenes, Arthrobacter, Azotobacter, Bacillus, Clostridium, Corynebacterium, Escherichia, Eubacterium, Flavobacterium, Methanobacillus, Methanosarcina, Mycobacterium, Propionibacterium, Proteus, Pseudomonas, Rhizobium, Rhodopseudomonas, Salmonella, Serratia, Streptococcus, Streptomyces and Xanthomonas.

26. The process according to claim 19, wherein said cells are of the genus Propionibacterium.

27. The process according to claim 19, wherein said disrupting is done by lysis of said cells.

28. The process according to claim 27, wherein said lysis is done by treatment selected from the group consisting of heat treatment, pasteurisation, treatment with bacteriolytic enzymes, mechanical disruption, and chemical treatment.

29. The process according to claim 27, wherein said lysis is done by a mixture of treatments selected from the group consisting of heat treatment, pasteurisation, treatment with bacteriolytic enzymes, mechanical disruption, and chemical treatment.

30. The process according to claim 27, which further comprises washing said cells prior to said lysis.

31. The process according to claim 30, wherein said washing is done by diafiltration.

32. The process according to claim 19, wherein said separation of said solid and liquid phases is effected by ultrafiltration or microfiltration.

33. The process according to claim 20, which further comprises drying said liquid phase.

34. The process according to claim 19, which further comprises washing said solid phase to obtain washings and combining said washings with said liquid phase.

35. The process according to claim 34, wherein said washing is done by diafiltration.

36. The process according to claim 1, wherein said preparation of natural vitamin B12 comprises natural vitamin B12 in an amount greater than 0.1% (w/w) based on the dry matter content of the preparation.

37. The process according to claim 19, wherein said mixture of natural vitamin B12 comprises natural vitamin B12 in an amount greater than 0.1% (w/w) based on the dry matter content of the preparation.

38. The process according to claim 19, wherein said mixture of natural vitamin B12 shows reduced segregation of vitamin B12 from the carrier during processing.

* * * * *